United States Patent [19]

Camerman et al.

[11] 4,002,685

[45] Jan. 11, 1977

[54] PROCESS FOR THE OXIDATION OF SECONDARY ALCOHOLS INTO KETONES

[75] Inventors: Philippe Jean Andre Charles Camerman, Wesembeek-Oppem; Jacques Daniel Victor Hanotier, Uccle, both of Belgium

[73] Assignee: Labofina S. A., Brussels, Belgium

[22] Filed: May 10, 1971

[21] Appl. No.: 141,988

[30] Foreign Application Priority Data

Jan. 27, 1971 Belgium .............................. 95993

[52] U.S. Cl. ........................... 260/593 R; 260/596
[51] Int. Cl.$^2$ ....................................... C07C 45/16
[58] Field of Search .................. 260/593 R, 596

[56] References Cited

UNITED STATES PATENTS

| | | | |
|---|---|---|---|
| 1,460,876 | 7/1923 | Williams et al. | 260/596 |
| 1,978,619 | 10/1934 | Bloomfield et al. | 260/596 X |
| 2,083,877 | 6/1937 | Steck et al. | 260/596 X |
| 2,287,803 | 6/1942 | Hull | 260/596 |
| 2,354,683 | 8/1944 | Hull | 260/596 |
| 2,725,400 | 11/1955 | Mecorney et al. | 260/596 X |
| 2,891,095 | 6/1959 | Opitz et al. | 260/596 |
| 3,080,426 | 3/1963 | Kirshenbaum et al. | 260/596 |

Primary Examiner—Donald G. Daus
Assistant Examiner—D.B. Springer

[57] ABSTRACT

A process for the oxidation of aliphatic secondary alcohols having no tertiary hydrogen on a carbon atom in alpha position relative to the carbon atom linked to the hydroxyl group, with selective formation of ketones having the same number of carbon atoms, said process comprising contacting said alcohols with a cobalt salt having a trivalent cobalt to total cobalt ratio of between 0.5 and 1, the concentration of said cobalt salt being at least 0.05 mole per liter of reaction mixture, at a temperature between 20° and 120° C.

10 Claims, No Drawings

PROCESS FOR THE OXIDATION OF SECONDARY ALCOHOLS INTO KETONES

The present invention relates to a process for the oxidation in the liquid phase of aliphatic secondary alcohols with selective formation of ketones. More particularly, the invention relates to a process whereby alcohols having the hydroxyl group at position 2 on the carbon chain may be oxidized preferentially from a mixture of secondary alcohols.

During the last years, aliphatic alcohols have become of great importance, particularly as intermediates for the synthesis of detergents, plasticizers, synthetic fibers, etc. . . . Many processes have thus been developed for their manufacture, especially by hydration of olefins or by oxidation of aliphatic hydrocarbons. For example, oxidation of straightchair paraffins in the presence of boric acid is used to produce secondary alcohols, which are obtained as a statistical mixture of all possible isomers. As a result of this development, aliphatic alcohols are now available for new uses in increasing amounts and at decreasing costs.

Oxidation is one of the most direct ways to transform aliphatic alcohols and many works have been done in this field. They have shown that in general these alcohols are relatively inert in autoxidation reactions wherein they may even behave as inhibitors. As a matter of fact, this method has only been applied in some particular cases such as the oxidation of 2-propanol into acetone and hydrogen peroxide. In most other cases, the autoxidation of aliphatic alcohols results in an extensive formation of lower acids by breaking of the carbon chain so that the method is not commercially feasible. Other processes have been suggested, such as the oxidation through inorganic agents such as potassium permanganate or chromic acid.

Although some of these methods are effective for the oxidation of secondary alcohols into ketones in general, they have never been used for industrial purposes either because an extensive breaking of the carbon chain also takes place or because the reaction requires an expensive consumption of the oxidizing agent which is not easily regenerated.

An object of the present invention is to provide a process for the oxidation in high yields of aliphatic secondary alcohols into ketones having the same number of carbon atoms, thus without degradation of the carbon chain. Another object of the invention is to provide a process whereby this transformation is effected in particularly mild conditions with an oxidizing agent which is easily regenerated. Other objects and advantages of the invention will appear hereinafter.

The process of the present invention for the oxidation is the liquid phase of aliphatic secondary alcohols having no tertiary hydrogen on a carbon atom in alpha position relative to the carbon atom linked to the hydroxyl group, with selective formation of ketones having the same number of carbon atoms, comprises contacting said secondary alcohols with a cobalt salt having a trivalent cobalt to total cobalt ratio of between 0.5 and 1, concentration of said cobalt salt being at least 0.05 mole per liter of reaction mixture, at a temperature between 20° and 120 C.

Moreover, we have found — and this is another important and unexpected feature of the invention — that by applying these conditions to a statistical mixture of secondary alcohols having the same number of carbon atoms, the alcohol where the hydroxyl group is linked at position 2 on the carbon chain (2-hydroxyalkanes) is oxidized more quickly and in better yield than the other isomers.

Consequently, according to another aspect of the invention, the present process may be applied for the selective oxidation of an alpha-hydroxyalkane in admixture with other aliphatic secondary alcohols into the corresponding methylketone, by using the above conditions while limiting the conversion of the starting alcohols.

In the practice of the invention, it is not always essential to use a solvent for the reaction to be carried out in the liquid phase. In some cases, the cobalt salt is soluble in the alcohols to be oxidized and the reaction can take place in the solution thus obtained. In other cases, however, it is preferable to use a solvent in which both the cobalt salt and the alcohols are soluble, this solvent being substantially inert against oxidation in the conditions used. The lower fatty acids containing from 2 to 4 carbon atoms and their mixtures fulfill these conditions. Among these solvents, acetic acid is particularly advantageous.

The process of the present invention may also be applied when the reaction mixture comprises two phases: on one hand, the liquid mixture of secondary alcohols to be oxidized and, on the other hand, a solution of the cobalt salt in a solvent wherein the alcohols are not completely soluble. For example, the secondary alcohols may be emulsified with an aqueous solution of the cobalt salt or with a solution of the salt in a mixed solvent consisting of water and a lower fatty acid. With such a system, the alcohols may be used to extract the ketones formed in the reaction which are thus protected against further oxidation.

Contrary to many oxidation reactions, the conversion of secondary alcohols into ketones by the process of the present invention does not require the use of oxygen. In most cases, similar results are obtained in the presence of oxygen and under inert atmosphere, e.g. under nitrogen. Generally, the selectivity of the reaction for ketones is slightly better under inert atmosphere as less acids are formed than in the presence of oxygen. But, in the second case, the consumption of the oxidizing agent is slightly lower. Indeed, under nitrogen this consumption varies from 1.8 to 2.4 atom-grams of trivalent cobalt per mole of reacted alcohol, whereas this ratio is 1.4 to 1.7 in the presence of oxygen. Those skilled in the art will easily appreciate the advantages of both systems in any particular case.

Among the cobalt salts which can be used in the process of the invention, those of carboxylic acids are particularly suitable as they are satisfactorily soluble in both organic and aqueous media. In fact, the cobalt salt of any carboxylic acid may be used. However, the cobalt salts of the lower fatty acids, i.e., containing from 2 to 4 carbon atoms are particularly advantageous, as their cobaltic form is readily prepared from the corresponding cobaltous form. For example, cobaltic acetate can be prepared by co-oxidation of cobaltous acetate and acetaldehyde in acetic acid in the presence of oxygen.

In order to ensure efficient and selective oridation by the process of the present invention, the cobalt salt must be used in relatively high concentration, i.e. at least 0.05 mole per liter of reaction mixture. When the concentration is below this limit, the reaction is too slow for being of commercial interest. Moreover, although the outstanding reactivity of 2-hydroxyalkanes compared to other secondary alcohols is already observed with cobalt concentrations as low as 0.01 mole per liter, the best results are obtained with concentrations of at least 0.05 mole per liter and preferably at least 0.1 mole per liter. The concentration to be used in each particular case will easily be determined by those skilled in the art from economical and practical considerations, taking into account that the upper limit is the concentration corresponding to saturation of the reaction mixture in the conditions used.

In the process of the invention, the cobalt salt is actualy the oxidizing agent and not a catalyst. Therefore when contacted with the alcohols, the cobalt salt must be at least partially in the cobaltic form. As the alcohols are transformed into ketones, this cobaltic form is reduced into the cobaltous form, so that both species are always present in the reaction mixture. But we have found — and this is another important feature of the present invention — that when the cobalt salt is used in relatively high concentration, its oxidizing activity is the more pronounced as the proportion of cobaltic form is higher, this activity becoming almost negligible when both forms are present in equivalent amounts, even when the absolute concentration of the cobaltic form is still important. Accordingly, in order to secure a sufficient reaction rate, the trivalent cobalt to total cobalt ratio, i.e. Co(III)/total Co must be higher than 0.5 and preferably higher than 0.6. It will therefore be necessary to regenerate trivalent cobalt by reoxidizing the cobaltous salt formed in the reaction. For this purpose, different methods, well known by those skilled in the art, may be used. For example, the cobaltous salt may be oxidized by anodic oxidation or by chemical means, for instance by co-oxidation in the presence of oxygen with an easily oxidizable compond, such as acetaldehyde, benzaldehyde or methylethylketone. When the oxidation of secondary alcohols is carried out in the presence of oxygen, a particularly convenient process is to feed continuously acetaldehyde into the reaction mixture. When, on the contrary, the reaction is performed under an inert atmosphere, the regeneration of trivalent cobalt must be effected in a separate step.

Still another important and unexpected feature of the present invention is that, in the conditions as specified above, the selectivity of the process is still observed at temperatures as high as 120° C, thus close to those used in many conventional process where this selectivity is not observed. This is of great advantage as the optimum temperature for each specific case may be selected in a relatively large range, i.e. between 20° and 120° C, according to the reactivity of the substrate, its solubility in the reaction mixture and other specific aspects. In most cases, however, the optimum temperatures will be comprised between 30° and 100° C and still more frequently between 50° and 70° C.

In the conditions as specified above, the aliphatic secondary alcohols are selectively oxidized into ketones having the same number of carbon atoms. Moreover, the alpha hydroxyalkanes are oxidized in preference to other secondary alcohols so that the process of the present invention can be applied to the oxidation of alpha-hydroxyalkanes in admixture with other secondary alcohols in order to produce selectively the corresponding methylketones.

Both selectivities are observed whatever the length of the carbon chain of the alcohols may be, but it is plain that the latter is only noticeable with alcohols containing at least 5 carbon atoms.

As it will be apparent to those skilled in the art, the selective oxidation of alpha-hydroxyalkanes present in a mixture of secondary alcohols can only be realized by limiting the conversion of these alcohols. If not, the alpha-hydroxyalkanes will first be oxidized and then the reaction will extend progressively to the other secondary alcohols so that it will be obtained a mixture of ketones with an isomer distribution similar to that of the starting alcohols. Therefore, in order to oxidize selectively alpha-hydroxyalkanes from a mixture of alcohols, the conversion of these will be kept below 50% and still peferably below 30%.

For this end one method is obviously to limit the time of reaction. However, another method consists in limiting the proportion of the alcohols to the cobalt salt. As the alcohols are oxidized in fact by trivalent cobalt according to a determined stoichiometry, it is possible to calculate the ratio in which the reactants have to be contacted for obtaining any desired conversion. In this calculation it should be taken into account that, as explained hereinabove, the consumption of trivalent cobalt for the conversion of secondary alcohols into ketones is different according to the reaction being carried out in the presence of oxygen or under inert atmosphere. It should also be taken into account that only the fraction of trivalent cobalt in excess over the amount of divalent cobalt present in the cobalt salt can oxidze efficiently secondary alcohols in the conditions of the process. For each specific case, the man skilled in the art will easily make this calculation from the data which are given in the present description.

The aliphatic secondary alcohols that can be oxidized selectively into ketones by the present process may be straight-chain as well as branched-chain alcohols, provided that the latter have no tertiary hydrogen on a carbon atom in alpha position relative to the carbon atom linked to the hydroxyl group. Indeed, secondary alcohols with such a tertiary hydrogen and having the formula

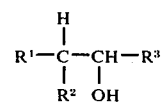

where $R_1$, $R_2$ and $R_3$ are hydrocarbon radicals, undergo chain breaking with formation of the acids $R_3$ — COOH.

The ketones prepared by the process of the present invention have many industrial uses, e.g. as solvents, plasticizers, aromas, etc...

These features and some other characteristics of the process of the present invention will be apparent from the following examples which are given by way of illustration and not as limitations on the scope of the invention.

EXAMPLE 1

This example illustrates the oxidation of a mixture of secondary heptanols, distributed in statistical manner, into ketones and more particularly into 2-heptanone.

A solution containing 0.65 mole per liter of cobalt acetate in acetic acid and with a Co(III)/total Co ratio of 0.90 was heated up to 60° C. A mixture of secondary heptanols comprising 40% of isomer 2, 40% of isomer 3 and 20% of isomer 4 was then added up to a final concentration of 0.50 mole per liter. The concentration of the cobalt salt in the resulting solution was 0,60 mole per liter and thus the molar ratio of cobalt to alcohols was 1.2. This solution was stirred at 60° C in the presence of oxygen at atmospheric pressure. After 3 hours, the reaction was stopped by reducing the cobaltic ions with an aqueous solution of a ferrous salt.

The reaction products were extracted with ether, then fractionated into acidic and non-acidic components by treatment of the extract with alkali and both fractions were analyzed separately by vapor-phase chromatography.

It was thus shown that 30% of the starting heptanols had been converted into oxidation products whose molar proportions, based on the amount of converted alcohols, are the following:
heptanones: 88% (isomer 2: 72%; 3: 19%; 4: 9%)
acids: 9%
others: 3%

Moreover by determining the cobaltic ions present in the system after reaction it was shown that about 1.7 atom-grams of trivalent cobalt had been consumed per mole of converted alcohol.

It is plain that by working in the conditions of the present invention, a mixture of secondary alcohols is mainly converted into heptanones with selective formation of 2-heptanone and relatively low consumption of oxidizing agent.

EXAMPLE 2

This example illustrates the oxidation of a mixture of secondary heptanols in the absence of oxygen.

The procedure of example 1 was repeated, but under an atmosphere of nitrogen instead of oxygen.

It was shown that 23% of the alcohols had been converted into oxidation products whose molar proportions, based on the amount of converted alcohols, are the following:
heptanones: 92% (isomer 2: 73%; 3: 19%; 4: 8%)
acids: 4%
others: 4%

Moreover, it was determined that about 2.4 atom-grams of trivalent cobalt had been consumed per mole of converted alcohol.

By comparing these results with those of the preceding example it is seen that the proportion of alcohols converted into acids is lower in the absence than in the presence of oxygen but that the consumption of oxidizing agent is slightly higher.

EXAMPLE 3

This example illustrates the influence of increasing the proportion of cobalt salt to the alcohols.

A solution containing 0.82 mole per liter of cobalt acetate in acetic acid and with a Co(III)/total Co ratio of 0.90 was heated up to 60° C under nitrogen atmosphere. A mixture of secondary heptanols having the same composition as in the preceding examples was then added up to a final concentration of 0.20 mole per liter. The concentration of the cobalt salt in the resulting solution was 0.80 mole per liter and thus the molar ratio of cobalt to alcohols was 4.0 instead of 1.2 as in the preceding examples. The experiment was then continued under nitrogen atmosphere as in Example 2.

It was shown that 60% of the starting alcohols had been converted into oxidation products whose molar proportions, based on the amount of converted alcohols, are the following:
heptanones: 92% (isomer 2: 62%; 3: 26%; 4: 12%)
Acids: 6%
others: 2%

Moreover it was determined that about 2.3 atom-grams of trivalent cobalt had been consumed per mole of converted alcohol.

By comparing these results with those of Example 2 it is seen that by increasing the proportion of the cobalt salt to the alcohols, the conversion of these can be increased without altering the proportion of ketones in the oxidation products nor the consumption of oxidizing agent. However, as expected, the selectivity for 2-heptanone is lower.

EXAMPLE 4

This example illustrates the oxidation of secondary heptanols in the presence of another cobalt salt than the acetate.

The procedure of Example 1 was repeated except that cobalt propionate was substituted for cobalt acetate.

The results were similar to those of Example 1.

EXAMPLE 5

This example illustrates the effect of temperature on the oxidation of secondary heptanols by the process of the present invention.

The procedure of Example 1 was repeated except that the reaction mixture was heated up to 100° C instead of 60° C and that the reaction was stopped after only 15 minutes.

It was shown that 30% of the starting alcohols had been converted into oxidation products whose solar proportions, based on the amount of converted alcohols, are the following:
heptanones: 84% (isomer 2: 66%; 3: 23%; 4: 11%)
acids: 15%
others: 1%

Moreover, about 1.4 atom-grams of trivalent cobalt had been consumed per mole of converted alcohol.

It is seen that these results are similar to those of Example 1, which shows that the characteristic selectivity of the process is still observed at temperatures as high as 100° C.

EXAMPLE 6

This example illustrates the influence of the concentration of the cobalt salt on the oxidation of secondary heptanols by the process of the present invention.

The procedure of Example 5 was repeated except that the final concentration of the cobalt salt was 0.05 instead of 0.6 mole per liter of reaction mixture.

It was shown that 5% of the alcohols had been converted into oxidation products whose molar proportions, based on the amount of converted alcohols, are the following:
heptanones: 83% (isomer 2: 56%; 3: 30%, 4: 14%)
acids: 11%
others: 6%

By comparing these results with those of Example 5, it is seen that a decrease of the concentration of the cobalt salt results in a decrease of both the reaction rate and the selectivity for 2-heptanone.

EXAMPLE 7

This example illustrates the oxidation of secondary heptanols in the presence of a solvent other than acetic acid.

The procedure of Example 1 was repeated except that propionic acid was substituted for acetic acid.

It was shown that the reaction products were mainly heptanones, with a 79% proportion of 2-heptanone.

EXAMPLE 8

This example illustrates the oxidation of a statistical mixture of secondary decanols into ketones and preferentially into 2-decanone.

The procedure of Example 1 was repeated from a mixture of secondary decanols containing 25% of each of the isomers 2,3,4 and 5. It was shown that 25% of the decanols had been converted into oxidation products whose molar proportions, based on the amount of converted alcohols, are the following:

decanones: 90% (isomer 2: 56%; 3: 16%; 4 +5: 28%)
acids: 9%
others: 1%

It is plain that by the process of the present invention secondary decanols are also converted into ketones in high yield and with selective production of 2-decanone.

EXAMPLE 9

This example illustrates the oxidation of 5-methyl-2-hexanol into 5-methyl-2-hexanone.

A solution containing 0.65 mole per liter of cobalt acetate in acetic acid and with a Co(III)/total Co ratio of 0.91 was heated up to 60° C under a nitrogen atmosphere. 5-methyl-2-hexanol was then added up to a final concentration of 0.50 mole per liter. After 1 hour at 60° C under nitrogen atomsphere, the reaction mixture was treated and analyzed as described in Example 1.

It was shown that 21% of the alcohol had been converted into oxidation products whoe molar proportions, based on the amount of converted alcohol, are the following:

5-methyl-2-hexanone: 91%
acids: 3%
others: 6%

Moreover, it was determined that 2.4 atom-grams of trivalent cobalt had been consumed per mole of converted alcohol.

By comparing these results with those of Example 2, it is seen that branched-chain alcohols are oxidized in the same way as straight-chain alcohols.

EXAMPLE 10

This example illustrates the oxidation of 5-methyl-2-hexanol in admixture with two of its isomers.

The procedure of Example 9 was repeated from an equimolar mixture of 5-methyl-2-hexanol with its isomers 5-methyl-3-hexanol and 2-methyl-3hexanol.

It was shown that 14% of the starting 5-methylhexanols had been converted into oxidation products whose molar proportions, based on the amount of converted 5-methylhexanols, are the following:

5-methylhexanones: 81% (isomer 2: 83%; 3: 17%)
acids: 10%
others: 9%

It can be seen that the 5-methylhexanols present in the starting mixture were oxidized in the same way as straight-chain alcohols with a particularly high selectivity for 5-methyl-2hexanone.

On the contrary, 25% of 2-methyl-3-hexanol were converted into butyric acid, which shows that secondary alcohols having a tertiary hydrogen on a carbon atom in alpha position relative to the carbon atom linked to the hydroxyl group undergo chain breaking in the conditions of the present process.

What is claimed is:

1. A process for the oxidation of 2-hydroxyalkane present in a mixture of aliphatic secondary alcohols having no tertiary hydrogen on a carbon atom in alpha position relative to the carbon atom linked to the hydroxyl group, to produce a reaction product containing at least about 80 mole % of ketones having the same number of carbon atoms and having a higher proportion of methyl ketone than the proportion of 2-hydroxyalkane in said mixture, said process comprising contacting said mixture of alcohols in the liquid phase with a cobalt salt of a lower fatty acid having a trivalent cobalt to total cobalt ratio of between 0.5 and 1, the concentration of said cobalt salt being at least 0.05 mole per liter of reaction mixture, at a temperature between 20° and 120° C. and limiting the conversion of said alcohols to at most 50%.

2. The process of claim 1, wherein said cobalt salt is cobalt acetate.

3. The process of claim 1 wherein the oxidation is performed in the presence of oxygen.

4. The process of claim 1 wherein the oxidation is performed in the absence of oxygen.

5. The process of claim 1 wherein said trivalent cobalt to total cobalt ratio is between 0.6 and 1.

6. The process of claim 1 wherein said temperature is within the range of 30° to 100° C.

7. The process of claim 1, wherein said step of limiting conversion of said alcohols comprises limiting the time of reaction.

8. The process of claim 1, wherein said step of limiting conversion of said alcohols comprises limiting the proportion of alcohols to said cobalt salt.

9. The process of claim 1 wherein the oxidation is performed in the presence of a solvent consisting of a lower fatty acid having from 2 to 4 carbon atoms or a mixture of such acids.

10. The process of claim 9 wherein said solvent is acetic acid.

* * * * *